(12) United States Patent
Mallela et al.

(10) Patent No.: US 8,394,956 B2
(45) Date of Patent: Mar. 12, 2013

(54) PROCESS FOR PREPARING PYRIMIDINE PROPENALDEHYDE

(75) Inventors: Sambhu Prasad Sarma Mallela, Hyderabad (IN); Sukumar Nandi, Hyderabad (IN); Gangadhara Bhima Shankar Nangi, Hyderabad (IN); Rani Ananta, Hyderabad (IN); Sivakumaran Meenakshisunderam, Hyderabad (IN)

(73) Assignee: Aurobindo Pharma Ltd., Hydarabad (IN)

( * ) Notice: Subject to any disclaimer, the term of this patent is extended or adjusted under 35 U.S.C. 154(b) by 40 days.

(21) Appl. No.: 12/998,195

(22) PCT Filed: Sep. 23, 2009

(86) PCT No.: PCT/IB2009/006935
§ 371 (c)(1), (2), (4) Date: Mar. 24, 2011

(87) PCT Pub. No.: WO2010/038124
PCT Pub. Date: Apr. 8, 2010

(65) Prior Publication Data
US 2011/0178296 A1    Jul. 21, 2011

(30) Foreign Application Priority Data
Sep. 30, 2008  (IN) .......................... 2411/CHE/2008

(51) Int. Cl.
*C07D 239/02*  (2006.01)

(52) U.S. Cl. ........................ 544/297; 514/275

(58) Field of Classification Search .................. 544/297
See application file for complete search history.

(56) References Cited

U.S. PATENT DOCUMENTS

| 6,844,437 | B1 | 1/2005 | Taylor |
| 8,049,010 | B2 * | 11/2011 | Huang ........................ 544/297 |
| 2008/0161560 | A1 | 7/2008 | Deshpande |
| 2009/0124803 | A1 | 5/2009 | Deshpande |
| 2010/0029940 | A1 * | 2/2010 | Dandala et al. ............... 544/297 |
| 2010/0048899 | A1 * | 2/2010 | Dandala et al. ............... 544/332 |

FOREIGN PATENT DOCUMENTS

| CN | 1763015 A | * | 4/2006 |
| CN | 101100459 A | * | 1/2008 |
| WO | WO 2006076845 A1 | * | 7/2006 |
| WO | WO 2006100689 A1 | * | 9/2006 |
| WO | WO 2008072078 A1 | * | 6/2008 |
| WO | WO 2008053334 A3 | * | 7/2008 |

OTHER PUBLICATIONS

M.B. Smith et al., March's Advanced Organic Chemistry Reactions, Mechanisms and Structure 705-728, 724-725 (2007).*
J.J. Li, Name Reactions a Collection of Detailed Reactions Mechanisms 603-604 (3rd ed., 2006).*

* cited by examiner

*Primary Examiner* — James O Wilson
*Assistant Examiner* — Alexander R Pagano
(74) *Attorney, Agent, or Firm* — Jay R. Akhave

(57) ABSTRACT

The present invention relates to an improved process for preparing (2E)-3-[4-(4-fluorophenyl)-6-isopropyl-2-(N-methyl-N-methylsulfonylamino)pyrimidin-5-yl]-propenal of formula (I), which is an useful intermediate in the preparation of Rosuvastatin.

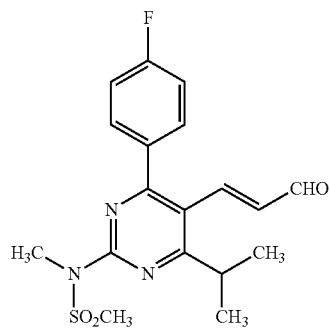

(I)

11 Claims, No Drawings

PROCESS FOR PREPARING PYRIMIDINE PROPENALDEHYDE

FIELD OF THE INVENTION

The present invention relates to an improved process for preparing (2E)-3-[4-(4-fluorophenyl)-6-isopropyl-2-(N-methyl-N-methylsulfonylamino)pyrimidin-5-yl]-propenal of formula I,

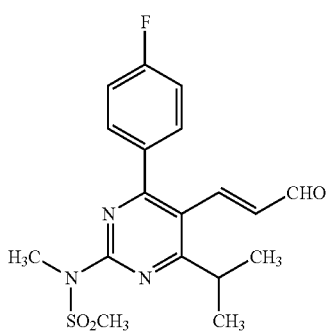

Formula I which is an useful intermediate in the preparation of bis[(E)-7-[4-(4-fluorophenyl)-6-isopropyl-2-[methyl(methylsulfonyl)amino]pyrimidin-5-yl]-3R,5S)-3,5-dihydroxyhept-6-enoicacid] calcium salt of Formula II.

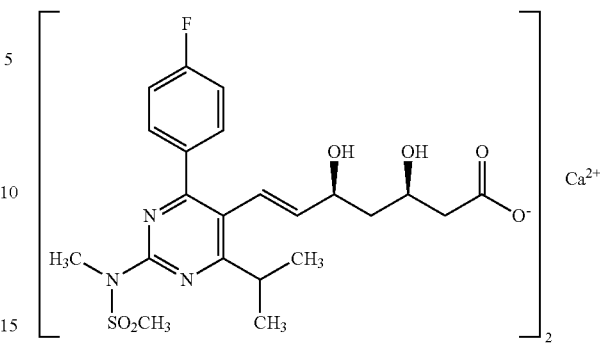

Formula II

BACKGROUND OF THE INVENTION

Rosuvastatin, which is an antihypercholesterolemic drug, is chemically known as (E)-7-[4-(4-fluorophenyl)-6-isopropyl-2-methyl(methylsulfonyl)amino]pyrimidin-5-yl]-(3R,5S)-3,5-dihydroxyhept-6-enoic acid calcium (2:1) salt of formula II. Rosuvastatin was for the first time disclosed in U.S. Pat. No. 5,260,440. Rosuvastatin is being marketed under the proprietary name CRESTOR, as an oral tablet, for the treatment of hypercholesterolemia. In view of the importance of Rosuvastatin as a lipid-lowering agent, several synthetic methods have been reported in the literature to prepare rosuvastatin, some of which are summarized below:

U.S. Pat. No. 5,260,440 discloses a process for preparing Rosuvastatin in examples. The process is as shown below:

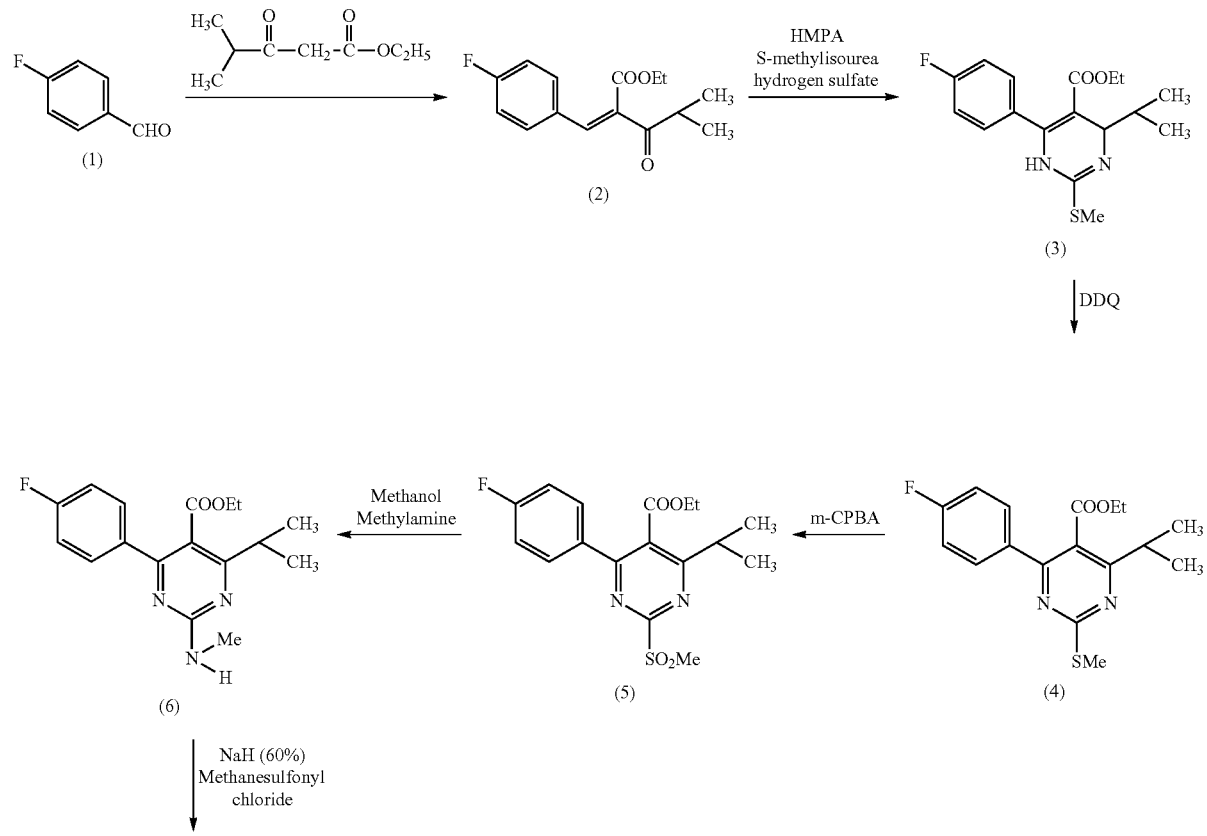

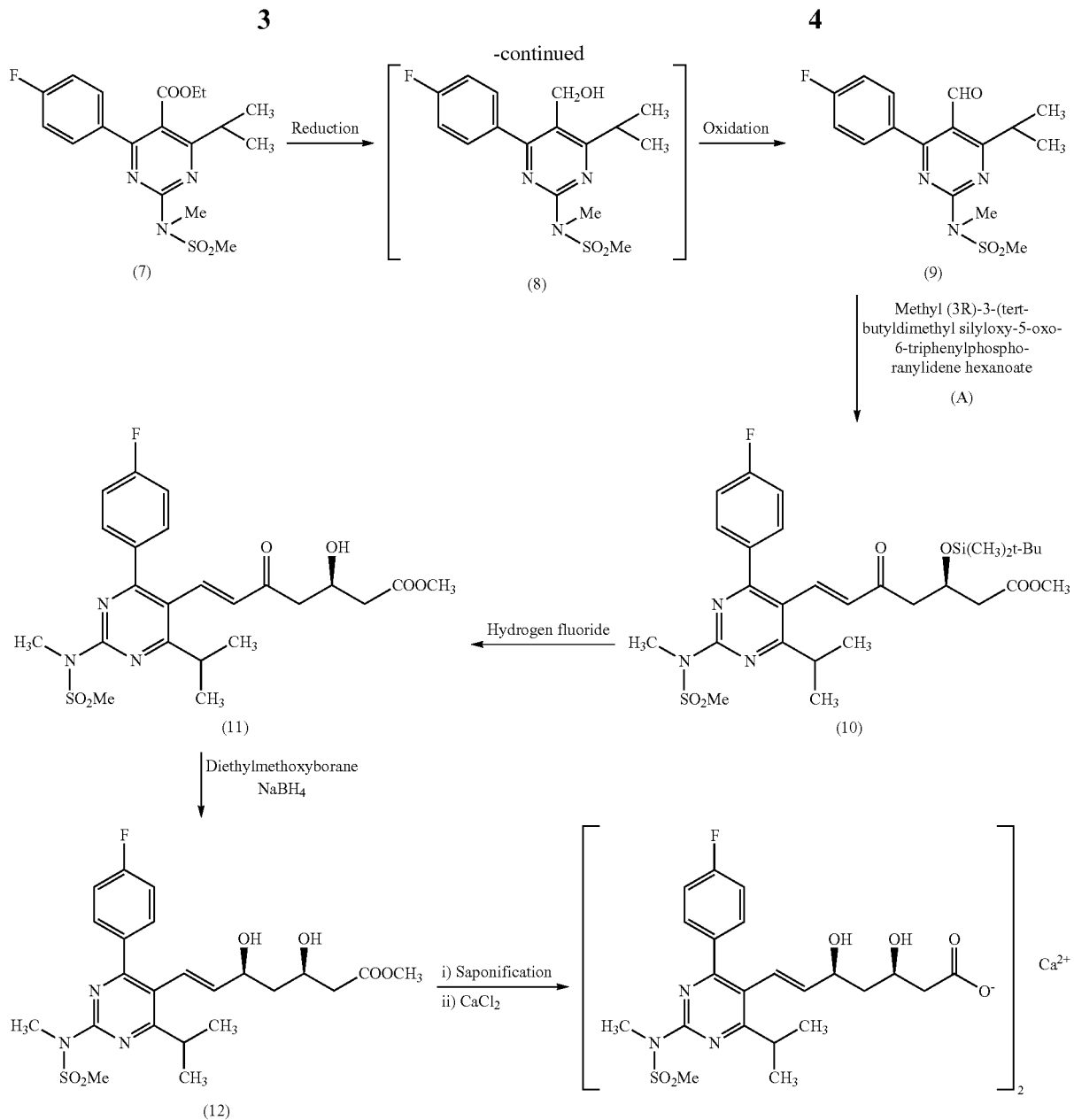

The difficulties in the above process are that the intermediate (A) is not obtained in pure form and its purification is tedious and overall yield is extremely low. Even, when intermediate (A) is not obtained in pure form, further condensation with intermediate (8) to form Rosuvastatin, which does not result in Rosuvastatin of right quality as the product contains unacceptable quantity of impurity levels.

WO 2000/049014 A1 describes a novel chemical process for the preparation of ter-butyl (E)-(6-{2-[4-(4-fluorophenyl)-6-isopropyl-2-methyl(methylsulfonyl)amino]-pyrimidin-5-yl]vinyl}-(4R,6S)-2,2-dimethyl[1,3]dioxan-4-yl)acetate, which comprises reacting diphenyl-{4-(4-fluorophenyl)-6-isopropyl-2-[methyl(methyl-sulfonyl)amino]pyrimidin-5-ylmethyl}phosphineoxide with tert-butyl 2-[(4R,6S)-6-formyl-2,2-dimethyl-1,3-dioxan-4-yl]acetate and its further conversion to rosuvastatin.

WO 2003/097614 A2 describes a modified procedure for the preparation of the starting material 4-(4-fluorophenyl)-6-isopropyl-2-[methyl(methylsulfonyl)amino]-pyrimidin-5-carboxaldehyde and further conversion to rosuvastatin by condensing with methyl (3R)-3-[(ter-butyldimethylsilyl)oxy]-5-oxo-6-triphenylphosphoranylidene hexanoate. The condensed product was deprotected using methanesulfonic acid and subsequently converted to Rosuvastatin calcium (2:1) salt.

WO 2004/014872 A1 describes a process for the manufacture of Rosuvastatin calcium (2:1) salt, which comprises mixing a solution of calcium chloride with a solution of water soluble salt of (E)-7-[4-(4-fluorphenyl)-6-isopropyl-2-[methyl(methylsulfonyl)amino]pyrimidin-5-yl]-(3R,5S)-3,5-dihydroxy-hept-6-enoic acid. This process for the preparation of Rosuvastatin employs the use of phosphorane side chain, the preparation of side chain requires eight synthetic steps and involves expensive reagents. This process is uneconomical and time consuming, hence not appropriate for commercial scale operation.

WO 2006/100689 A1 discloses a process for preparation of Rosuvastatin, which is as shown below:

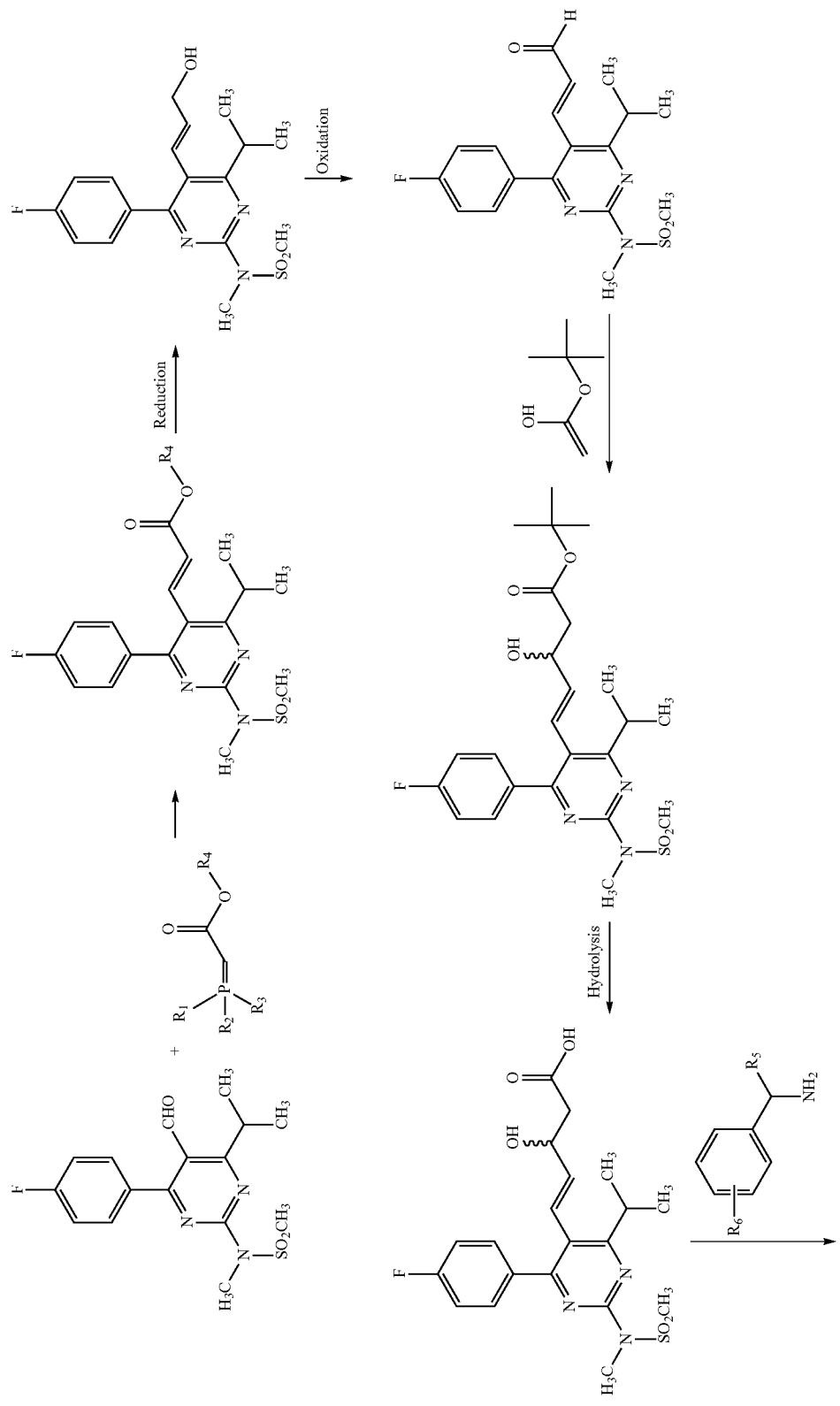

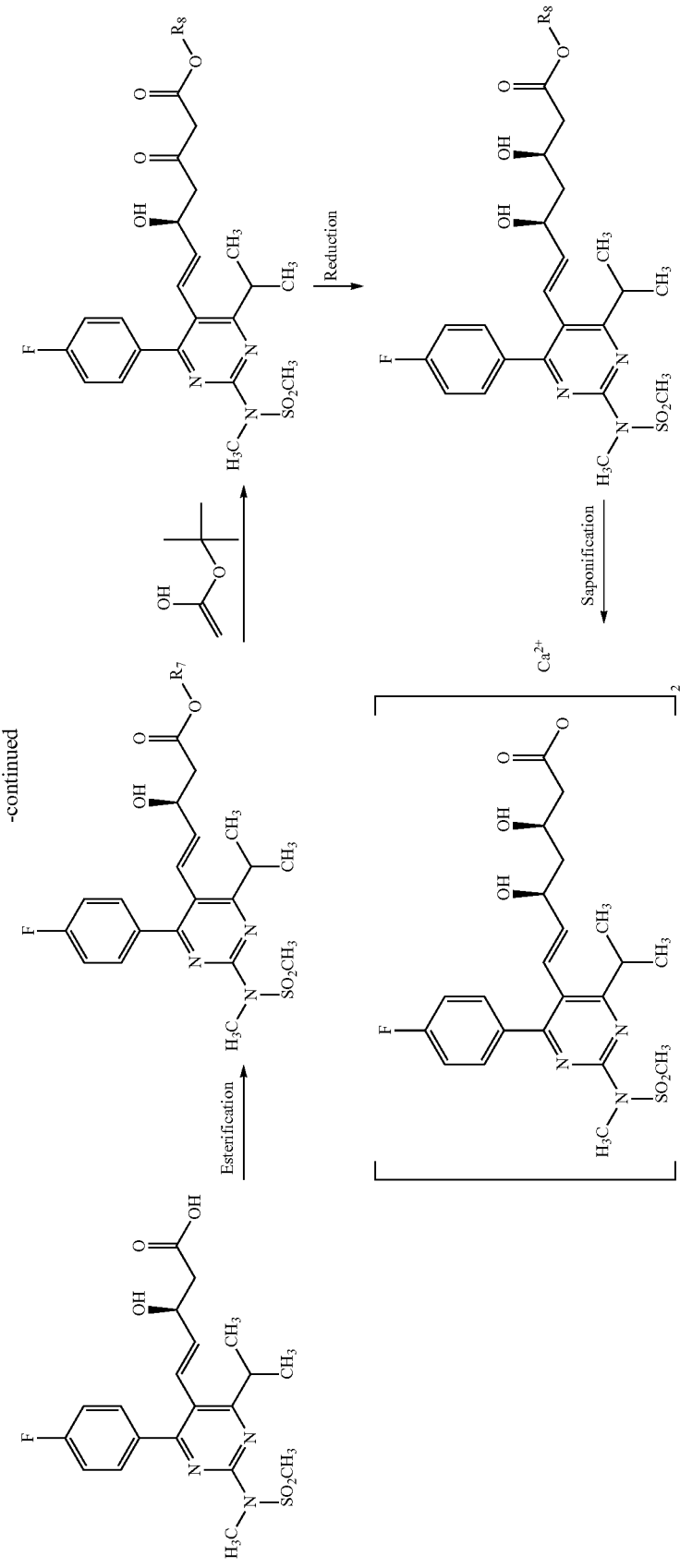

In the above scheme, $R_1$, $R_2$, $R_3$ represents substituted or unsubstituted phenyl and $R_4$ represents an aliphatic residue selected from $C_{1-4}$ alkyl; $R_5$ represents $C_{1-4}$ alkyl which is optionally substituted by hydroxyl; $R_6$ represents hydrogen, halogen, $C_{1-4}$ alkyl or $C_{1-4}$ alkoxy; $R_7$ represents aliphatic residue and $R_8$ represents $C_{1-4}$ alkyl.

WO 2006/106526 A1 describes the preparation of Rosuvastatin, which is as shown below:

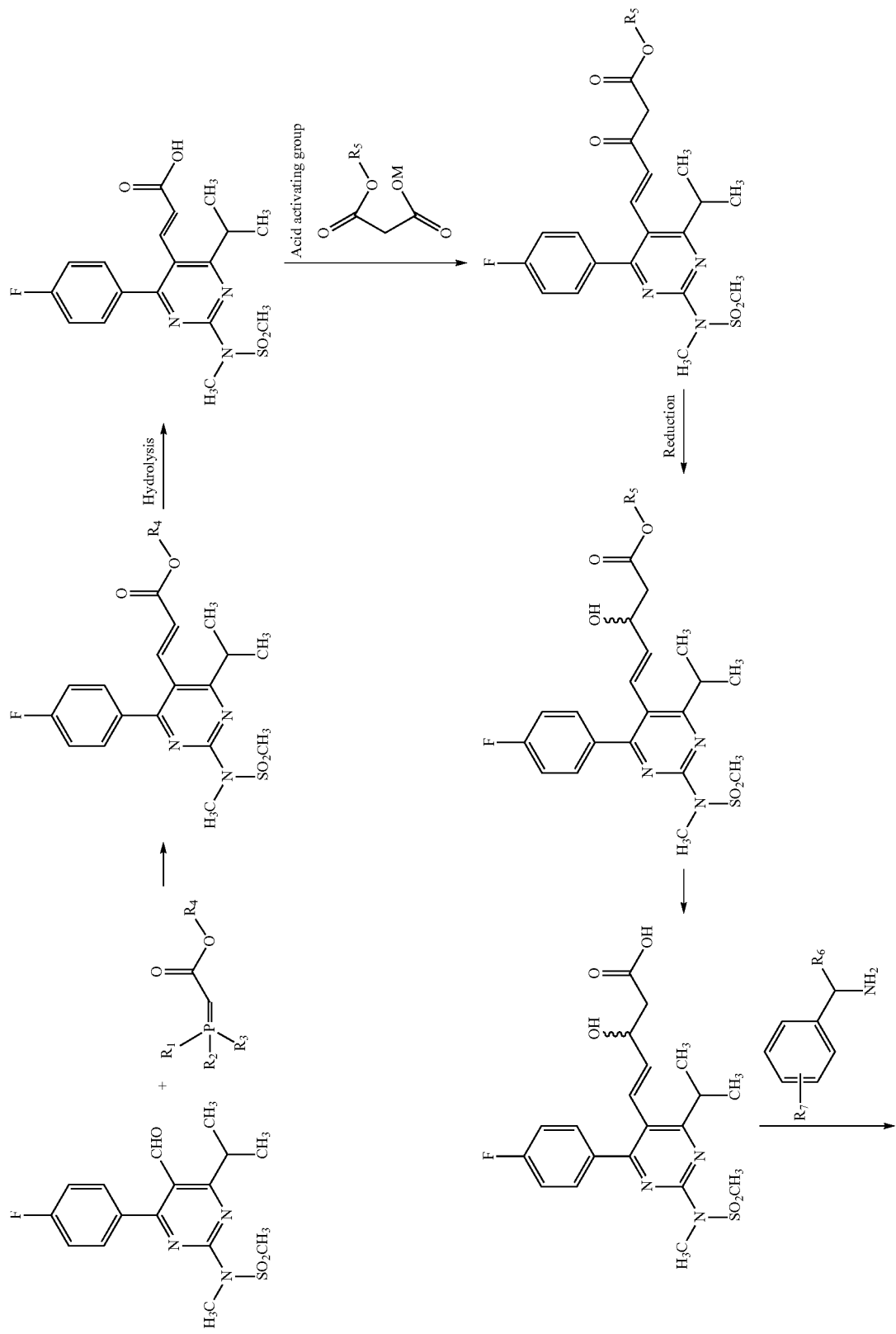

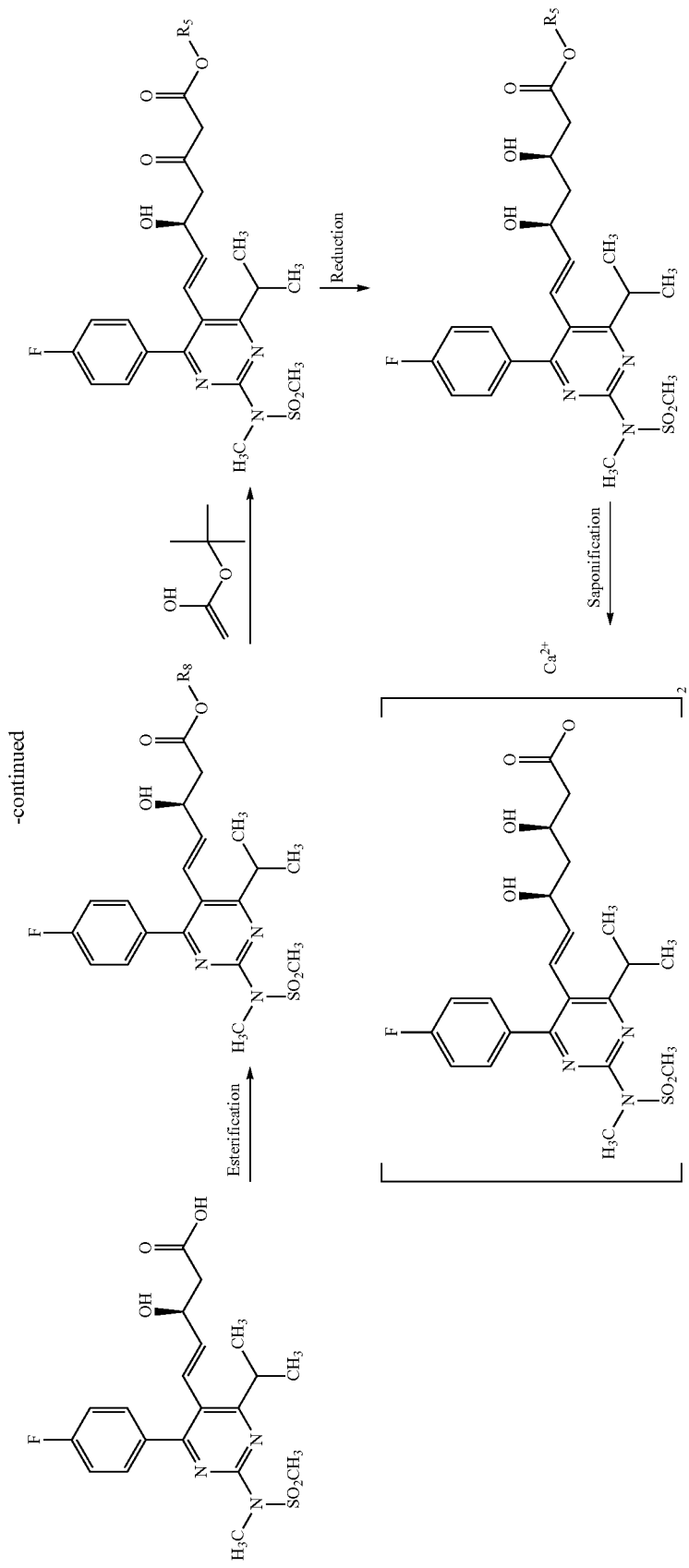

In the above mentioned scheme, $R_1$, $R_2$, $R_3$ are substituted or unsubstituted phenyl and $R_4$ is an aliphatic residue selected from $C_{1-4}$ alkyl; $R_5$ represents $C_{1-4}$ alkyl, M is an alkali metal salt. X represents a halogen; $R_6$ represents $C_{1-4}$ alkyl, which is optionally substituted by hydroxyl; $R_7$ represents hydrogen, halogen, $C_{1-4}$ alkyl or $C_{1-4}$ alkoxy; $R_8$ is an aliphatic residue selected from $C_{1-4}$ alkyl.

WO 2006/076845 A1 describes a process to prepare Rosuvastatin and its salt thereof, which is as shown below:

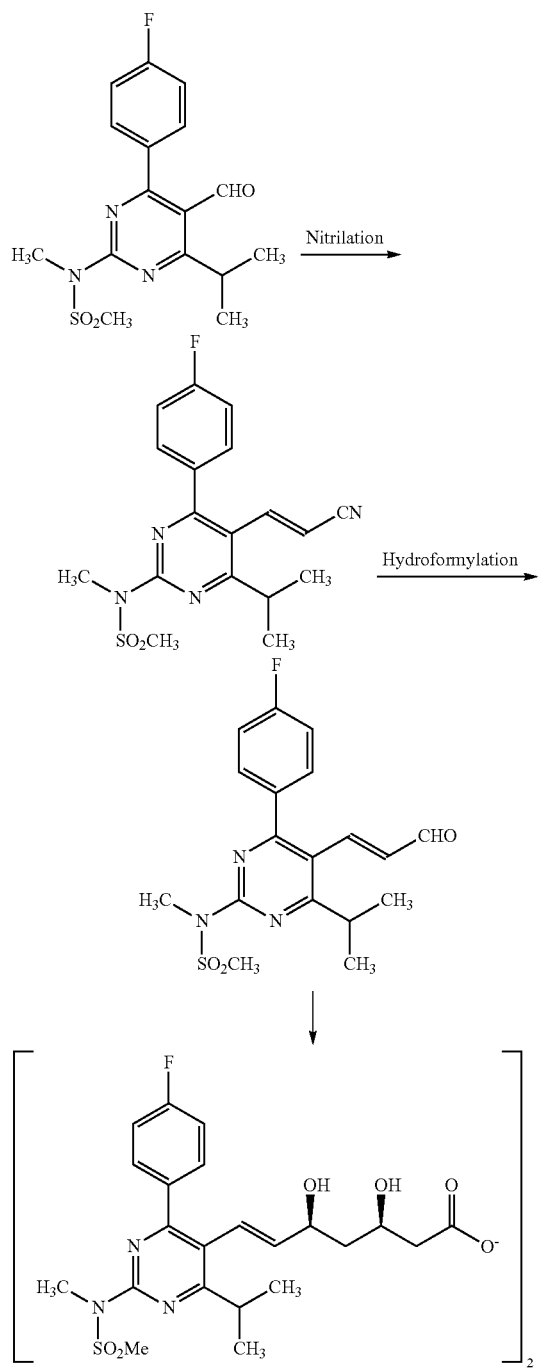

We have now found an improved process to prepare (2E)-3-[4-(4-fluorophenyl)-6-isopropyl-2-(N-methyl-N-methylsulfonylamino)pyrimidin-5-yl]propenal of Formula I and subsequently converting the compound of Formula I to Rosuvastatin and its pharmaceutically acceptable salts thereof of Formula II.

Objective

The main objective of the present invention is to provide an improved process for preparing (2E)-3-[4-(4-fluorophenyl)-6-isopropyl-2-(N-methyl-N-methylsulfonyl-amino)pyrimidin-5-yl]propenal, which is an useful intermediate in the preparation of Rosuvastatin.

Yet another objective of the present invention is to provide an improved process for preparing (2E)-3-[4-(4-fluorophenyl)-6-isopropyl-2-(N-methyl-N-methylsulfonyl-amino)pyrimidin-5-yl]propenal, which is simple, industrially applicable and economically viable.

Another objective of the present invention is to provide a process for a novel intermediate that is used in the preparation of rosuvastatin calcium.

SUMMARY OF THE INVENTION

The present invention relates to, an improved process for the preparation of (2E)-3-[4-(4-fluorophenyl)-6-isopropyl-2-(N-methyl-N-methylsulfonylamino)pyrimidin-5-yl]-propenal of Formula I,

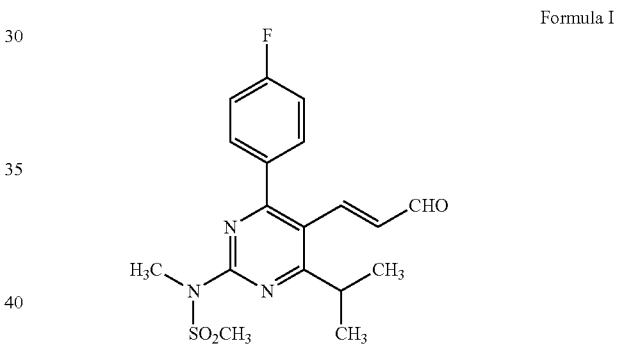

Formula I which comprises:

a) treating 4-(4-fluorophenyl)-6-isopropyl-2-(N-methyl-N-methylsulfonyl-amino)pyrimidin-5-yl]carboxaldehyde of Formula III,

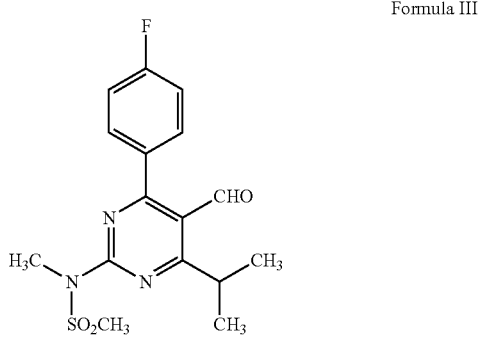 [SMILES: CC(C)c1nc(N(C)S(C)(=O)=O)nc(-c2ccc(F)cc2)c1C=O]

Formula III with an organometallic reagent to obtain a mixture of substituted ethanol of Formula IV and an olefin of Formula V;

Formula IV

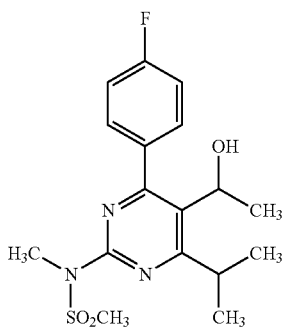

Formula V

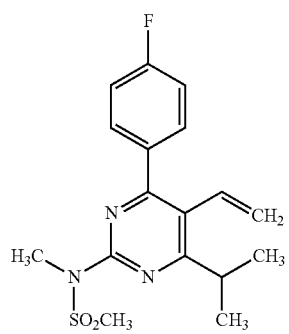

b) treating the mixture obtained above with Vilsmeier reagent; and
c) isolating the compound of Formula I.

In another embodiment of the present invention, the (2E)-3-[4-(4-fluorophenyl)-6-isopropyl-2-(N-methyl-N-methylsulfonylamino)pyrimidin-5-yl]propenal of Formula I, is converted to Rosuvastatin and its pharmaceutically acceptable salts thereof.

DETAILED DESCRIPTION OF THE INVENTION

The compound of Formula III is treated with organometallic reagent selected from $CH_3MX$ or $CH_3M$ or $(CH_3)_nM$; M represents magnesium, lithium, zinc, cadmium etc.; X represents chloro, fluoro, iodo, bromo; n represents an integer 1 or 2; in an inert solvent selected from tetrahydrofuran, ether, toluene and mixtures thereof, at a temperature ranging from 0-30° C., preferably 0-10° C., to give a mixture of substituted ethanol of Formula IV and olefin of Formula V. Optionally the mixture is separated. The mixture of Formula IV and Formula V or separated compound is treated with Vilsmeier reagent to give a compound of Formula I.

In another aspect of the present invention the molar ratio of organometallic reagent based on pyrimidine carboxaldehyde is 1-10, preferably 1-3 moles.

In yet another aspect of the present invention, the Vilsmeier reagent is prepared from N,N-dimethylformamide and phosphorous oxychloride or N,N-dimethylformamide and oxalyl chloride or N-methylformanilide and phosphorous oxychloride or N-methylformanilide and oxalyl chloride in the presence of a solvent, selected from the group dichloromethane, tetrachloromethane, 1,2-dichlorobenzene, ethylene dichloride, acetonitrile and optionally using an organic base. The organic base is selected from lutidine, tetramethylpyrazine, 2,6-dimethyl pyrazine.

In yet another aspect of the present invention, the Vilsmeier reagent can be prepared and added to the reaction mass or can be prepared in situ during the reaction.

In yet another aspect of the present invention, molar ratio of Vilsmeier reagent added to the reaction mass is ranging from 1 mole equivalent to 20 mole equivalents, preferably 8-15 mole equivalents based on compound of Formula IV.

In yet another aspect of the present invention, the compound of Formula IV is dehydrated to olefin compound of Formula V during the course of the reaction, because of which compound of Formula IV and compound of Formula V is formed. The mixture of compound of Formula IV and compound of Formula V were separated using column chromatography.

In yet another aspect of the present invention, the compound of the Formula I, is further converted to Rosuvastatin and its pharmaceutical acceptable salts thereof, by using the methods known in the art.

In an embodiment of the present invention, there is provided a novel intermediate, of Formula IV and Formula V Formula IV

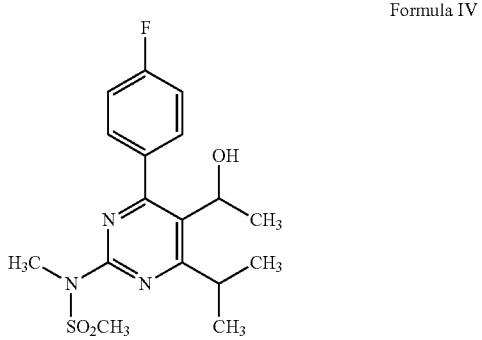 [SMILES: CC(C)c1nc(N(C)S(C)(=O)=O)nc(-c2ccc(F)cc2)c1C(C)O]

The Formula IV is characterized by 1H NMR (300 MHz, $CDCl_3$): δ (ppm): 1.33 (dd, J=6, 12 Hz; 6H, —$CH(CH_3)_2$), 1.58 (d, J=6 Hz, 3H, $CH_3$), 1.76 (d, J=4.5 Hz, 1H, —OH), 3.51 (S, 3H, —$NCH_3$), 3.54 (s, 3H, —$SO_2CH_3$), 3.82-3.87 (m, 1H, —$CH(CH_3)_2$), 5.14-5.17 (m, 1H, —CHOH), 7.12-7.18 (m, 2H, ArH), 7.45-7.5 (m, 2H, ArH)

Formula V

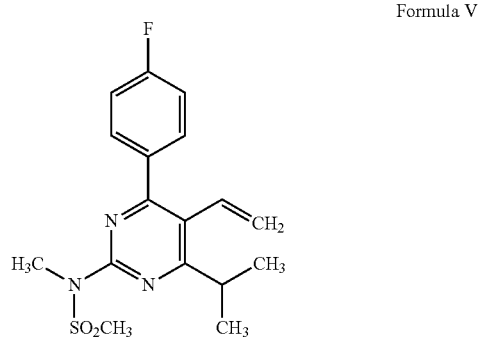 [SMILES: C=Cc1c(-c2ccc(F)cc2)nc(N(C)S(C)(=O)=O)nc1C(C)C]

The Formula V is characterized by $^1$H NMR (300 MHz, $CDCl_3$): δ (ppm): 1.29 (d, J=6 Hz, 6H, —$CH(CH_3)_2$), 3.44-3.51 (m, 1H, —$CH(CH_3)_2$), 3.54 (s, 3H, N—$CH_3$), 3.60 (s, 3H, —$SO_2CH_3$), 5.20 (dd, J=1.5, 17.7 Hz, 1H, =CH), 5.5 (dd, J=1.5, 11.4 Hz, 1H, CH=$CH_2$), 7.01-7.12 (m, 2H, ArH), 7.67-7.74 (m, 2H, ArH).

The invention is illustrated by the following examples, which are provided by way of illustration only and should not be construed to limit the scope of the invention.

EXAMPLE 1

Preparation of Mixture of 1-[4-(4-Fluorophenyl)-6-Isopropyl-2-[(N-Methyl-N-Methylsulfonyl)Amino]-Pyrimidin-5-Yl]-1-Hydroxy Ethane & 1-[4-(4-Fluorophenyl)-6-Isopropyl-2-[(N-Methyl-N-Methylsulfonyl)Amino]Pyrimidin-5-Yl]-Ethene Methyl magnesium chloride solution (3M) (11.87 ml, 0.0356 moles) in tetrahydrofuran was added to a pre-cooled suspension of pyrimidine carboxaldehyde (5 g, 0.0142 moles) in anhydrous tetrahydrofuran (30 ml) under stirring for 30 min at 0-5° C. The reaction mass was stirred at the same temperature. After completion of the reaction, the reaction mass was poured into pre-cooled saturated ammonium chloride solution (100 ml) at 0-5° C. and stirred for 1 h at 5-10° C. The product was extracted into ethyl acetate (150 ml) and washed with saturated aqueous sodium chloride solution. The organic layer was dried over anhydrous sodium sulfate and filtered. The filtrate was distilled under vacuum at 40-45° C. until the traces of ethyl acetate were completely removed to give the title compound.

Yield: 5.3 g

EXAMPLE 2

Preparation of 1-[4-(4-Fluorophenyl)-6-Isopropyl-2-[(N-Methyl-N-Methylsulfonyl)Amino]-Pyrimidin-5-Yl]-1-Hydroxy Ethane & 1-[4-(4-Fluorophenyl)-6-Isopropyl-2-[(N-Methyl-N-Methylsulfonyl)Amino]Pyrimidin-5-Yl]-Ethene Methyl magnesium chloride solution (3M) (11.87 ml, 0.0356 moles) in tetrahydrofuran was added to a pre-cooled suspension of pyrimidine carboxaldehyde (5 g, 0.0142 moles) in anhydrous tetrahydrofuran (30 ml) under stirring for 30 min at 0-5° C. The reaction mass was stirred at the same temperature. After completion of the reaction, the reaction mass was poured into pre-cooled dilute hydrochloric acid (100 ml, 10% v/v) at 5° C. and stirred for 1 h at 5-10° C. Ethyl acetate (100 ml) was added to the reaction mass and stirred for 10 min. The organic layer was separated and aqueous layer is extracted with ethyl acetate (50 ml). The organic extracts were combined and washed with DM water (50 ml) and with 5% saturated aqueous sodium chloride solution (30 ml). The organic layer was dried over anhydrous sodium sulfate and filtered. The filtrate was distilled under vacuum at 40-45° C. until the traces of ethyl acetate were completely removed to give crude 1-[4-(4-fluorophenyl)-6-isopropyl-2-[(n-methyl-n-methylsulfonyl)amino]-pyrimidin-5-yl]-1-hydroxy ethane & 1-[4-(4-fluorophenyl)-6-isopropyl-2-[(n-methyl-n-methylsulfonyl)amino]pyrimidin-5-yl]-ethene.

Yield: 5.2 g

The above obtained crude 1-[4-(4-fluorophenyl)-6-isopropyl-2-[(n-methyl-n-methylsulfonyl)amino]-pyrimidin-5-yl]-1-hydroxy ethane & 1-[4-(4-fluorophenyl)-6-isopropyl-2-[(n-methyl-n-methylsulfonyl)amino]pyrimidin-5-yl]-ethene was separated by column chromatography to give pure 1-[4-(4-fluorophenyl)-6-isopropyl-2-[(n-methyl-n-methylsulfonyl)amino]-pyrimidin-5-yl]-1-hydroxy ethane & 1-[4-(4-fluorophenyl)-6-isopropyl-2-[(n-methyl-n-methylsulfonyl)amino]pyrimidin-5-yl]-ethene.

Hydroxy ethane compound—1H NMR (300 MHz, CDCl$_3$): δ (ppm): 1.33 (dd, J=6, 12 Hz; 6H, —CH(CH$_3$)$_2$), 1.58 (d, J=6 Hz, 3H, CH$_3$), 1.76 (d, J=4.5 Hz, 1H, —OH), 3.51 (S, 3H, —NCH$_3$), 3.54 (s, 3H, —SO$_2$CH$_3$), 3.82-3.87 (m, 1H, —CH(CH$_3$)$_2$), 5.14-5.17 (m, 1H, —CHOH), 7.12-7.18 (m, 2H, ArH), 7.45-7.5 (m, 2H, ArH)

Ethene compound—$^1$H NMR (300 MHz, CDCl$_3$): δ (ppm): 1.29 (d, J=6 Hz, 6H, —CH(CH$_3$)$_2$), 3.44-3.51 (m, 1H, —CH(CH$_3$)$_2$), 3.54 (s, 3H, N—CH$_3$), 3.60 (s, 3H, —SO$_2$CH$_3$), 5.20 (dd, J=1.5, 17.7 Hz, 1H, =CH), 5.5 (dd, J=1.5, 11.4 Hz, 1H, CH=CH$_2$), 7.01-7.12 (m, 2H, ArH), 7.67-7.74 (m, 2H, ArH)

EXAMPLE 2

Preparation of (2E)-3-[4-(4-Fluorophenyl)-6-Isopropyl-2-(N-Methyl-N-Methylsulfonylamino)Pyrimidin-5-Yl]-Propenal Phosphorous oxychloride (10.03 g, 0.0654 moles) was added to pre-cooled N,N-dimethylformamide (4.85 g, 0.066 moles) under stirring at 5-10° C. and the contents were stirred for 30 min at 40-45° C. To this reagent, a crude mixture of alcohol IV and olefin V (2 g, 0.005 moles, in 5 ml of N,N-dimethylformamide and 1.168 g of lutidine) was added drop wise for 20 min while maintaining the temperature between 25 and 30° C. The reaction mass was stirred for 1 h at the same temperature. Thereafter, the temperature of the reaction mass was slowly raised to 70-75° C. and stirred at the same temperature for 26 h. After completion of the reaction, the reaction mass was cooled to 30° C. and poured into pre-cooled saturated sodium acetate solution (100 ml, 2° C.) and then stirred for 2 h at 20-25° C. To the aqueous solution, ethyl acetate (50 ml) was added and stirred for 10 min at 25-30° C. The resulting organic layer was washed with DM water (2×50 ml) and then concentrated to give the title compound.

Yield: 2 g

The above crude pyrimidine propenaldehyde (2 g) was chromatographed over silica gel using 5% ethyl acetate and hexanes as eluant to give the pure pyrimidine propenaldehyde.

Yield: 1.0 g

EXAMPLE 3

Preparation of (2E)-3-[4-(4-Fluorophenyl)-6-Isopropyl-2-(N-Methyl-N-Methylsulfonylamino)Pyrimidin-5-Yl]Propenal Phosphorous oxychloride (50.06 g, 0.326 moles) was added to pre-cooled N,N-dimethylformamide (23.86 g, 0.326 moles) under stirring at 5-10° C. The contents were stirred for 30 min at 40-45° C. To the reaction mass, a crude mixture of alcohol IV and olefin V (10 g, 0.0272 moles) in 20 ml of N,N-dimethylformamide was added drop wise in 20 min by maintaining the temperature at 25-30° C. The contents were stirred for 1 h at 25-30° C., then slowly raised the temperature of the reaction mass to 70-75° C. and stirred at the same temperature for 30 h. After completion of the reaction, the reaction mass was poured into pre-cooled DM water (250 ml, 2° C.), stirred for 30 min at 15-20° C. and then adjusted the pH to 7.8 with 25% aqueous sodium hydroxide solution (250 ml) at 15-20° C.

The resulting suspension was stirred for 30 min at 15-20° C. Ethyl acetate (150 ml) was added and stirred for 10 min at 15-20° C. The aqueous layer was back extracted with ethyl acetate (50 ml). The combined organic extracts were washed with DM water (2×250 ml). The resulting organic layer was then subjected to carbon treatment prior to distillation to obtain crude pyrimidine propenal.

Yield: 9.5 g

The above crude pyrimidine propenal was dissolved in ethanol (27 ml) and stirred for 20 h at 20-25° C. The resulting mass was cooled to 5° C. and stirred for 1 h at 0-5° C. The precipitated product was collected, washed with chilled ethanol (13 ml, −5° C.) and then dried under vacuum at 45° C. to give pure pyrimidine propenal.

Yield: 4.2 g

Chromatographic Purity (by HPLC): 94.56%

EXAMPLE 4

Preparation of (2E)-3-[4-(4-Fluorophenyl)-6-Isopropyl-2-(N-Methyl-N-Methylsulfonylamino)Pyrimidin-5-Yl]Propenal Phosphorous oxychloride (41.78 g, 0.272 moles) was added to pre-cooled N,N-dimethyl-formamide (19.89 g, 0.272 moles) under stirring at 5-10° C. The contents were stirred for 30 min at 40-45° C. To the reaction mass, a crude mixture of alcohol IV and olefin V (10 g) in 20 ml of N,N-dimethylformamide was added drop wise in 20 min maintaining the temperature at 25-30° C. The contents were stirred for 1 h at 25-30° C., then slowly raised the temperature to 70-75° C. and stirred at the same temperature for 18 h. After completion of the reaction, the reaction mass was poured into pre-cooled DM water (250 ml, 5° C.), stirred for 1 h at 15-20° C. and then adjusted the pH to 7.5 with 25% aqueous sodium hydroxide solution (180 ml) at 15-20° C. The product was extracted with ethyl acetate (150 ml) and washed with DM water (2×100 ml). The resulting organic layer was treated with carbon and filtered the solution through hyflo. The filtrate was concentrated under vacuum to give crude pyrimidine propenaldehyde.

Yield: 9.5 g

The crude pyrimidine propenaldehyde (9.5 g) was dissolved in ethyl acetate (20 ml) at 20-25° C. and then n-heptane (80 ml) was added. This mass was stirred for 2 h at 25-30° C. The resulting mass was cooled to 5° C. and stirred for 1 h at 0-5° C. After filtration the solid was washed with pre-cooled n-heptane (20 ml, 2° C.) and then dried under vacuum at 35° C. to give the pure pyrimidine propenaldehyde Yield: 6 g

EXAMPLE 5

Preparation of (2E)-3-[4-(4-Fluorophenyl)-6-Isopropyl-2-(N-Methyl-N-Methylsulfonylamino)Pyrimidin-5-Yl]Propenal Phosphorous oxychloride (8.35 g, 0.0545 moles) was added to N-methylformanilide (17.36 g, 0.0545 moles) under stirring at 5-10° C. The contents were stirred for 30 min at 40-45° C. To the reaction mass, a crude mixture of alcohol IV and olefin V (2 g, 0.0054 moles) was added in 5 min at 25-30° C. The contents were stirred for 1 h at 25-30° C., then slowly raised the temperature of reaction mass to 70-75° C. and stirred at the same temperature for 20 h. After completion of the reaction, the reaction mass was poured into pre-cooled DM water (100 ml, 2° C.), stirred for 1 h at 15-20° C. and then adjusted the pH to 7.5 with 25% aqueous sodium hydroxide solution (40 ml) at 15-20° C. The product was extracted into ethyl acetate (100 ml), charcolized and concentrated to yield 1.8 g of crude pyrimidine propenaldehyde as an oily mass.

The crude pyrimidine propenaldehyde (1.8 g) was dissolved in ethyl acetate (4 ml) and treated with n-heptane (32 ml). The reaction mass was stirred for 2 h at 25-30° C. The resulting mass was cooled to 5° C. and stirred for 30 min at 0-5° C. Filtered the mass, washed with pre-cooled n-heptane (4 ml, 0° C.) and then dried under vacuum at 35° C. to give the pure pyrimidine propenaldehyde.

Yield: 0.5 g

EXAMPLE 6

Preparation of (2E)-3-[4-(4-Fluorophenyl)-6-Isopropyl-2-(N-Methyl-N-Methylsulfonylamino)Pyrimidin-5-Yl]Propenal Phosphorous oxychloride (12.53 g, 0.081 moles) was added to pre-cooled N,N-dimethylformamide (5.96 g, 0.081 moles) under stirring at 5-10° C. The contents were stirred for 30 min at 40-45° C. To the reaction mass, a crude mixture of alcohol IV and olefin V (3 g) in methylene chloride (9 ml) was added in 10 min while maintaining the temperature at 25-30° C. The contents were stirred for 1 h at 25-30° C., then slowly raised the temperature to 60-65° C. and stirred at the same temperature for 40 h. After completion of the reaction, the reaction mass was poured into pre-cooled DM water (150 ml, 2° C.), stirred for 1 h at 15-20° C. and then the pH was adjusted to 8 with 25% aqueous sodium hydroxide solution (40 ml) at 15-20° C. The product was extracted with methylene chloride (150 ml), washed with DM water (2×100 ml), charcolized and concentrated to give crude pyrimidine propenaldehyde.

Yield: 3.05 g

The crude pyrimidine propenaldehyde (3 g) was stirred with ethyl acetate (6 ml) at 20-25° C. and then added n-heptane (24 ml). The mixture was stirred for 3 h at 25-30° C. The resulting mass was cooled to 5° C. and stirred for 30 min at 0-5° C. The precipitated mass was filtered, washed with chilled n-heptane (6 ml) and dried to give the pure pyrimidine propenaldehyde.

Yield: 1.6 g

Chromatographic Purity (by HPLC): 96.8%

EXAMPLE 7

Preparation of (2E)-3-[4-(4-Fluorophenyl)-6-Isopropyl-2-(N-Methyl-N-Methylsulfonylamino)Pyrimidin-5-Yl]Propenal Phosphorous oxychloride (20.89 g, 0.136 moles) was added to pre-cooled N,N-dimethylformamide (9.94 g, 0.136 moles) under stirring at 5-10° C. The contents were stirred for 30 min at 40-45° C. To the reaction mass, a crude mixture of alcohol IV and olefin V (5 g) dissolved in 10 ml of N,N-dimethylformamide was added drop wise in 15 min maintaining the temperature at 25-30° C. The contents were stirred for 1 h at 25-30° C., then slowly raised the temperature to 70-75° C. and stirred at the same temperature to complete the reaction (30 h). After completion of the reaction, cooled the reaction mass to 30° C., poured into pre-cooled DM water (250 ml), stirred for 1 h at 15-20° C. and then adjusted the pH to 8 with 25% aqueous sodium hydroxide solution (66 ml) at 15-20° C. Methylene chloride (50 ml) was added and stirred for 10 min at the same temperature. The layers were separated and the aqueous layer was back extracted with methylene chloride (35 ml). The combined organic extracts were washed with DM water (2×50 ml). The resulting organic layer was then subjected to carbon treatment. Filtered the mass through hyflo, washed with methylene chloride (30 ml) and the resulting filtrate was distilled under vacuum until the traces of methylene chloride were completely removed to give crude pyrimidine propenaldehyde.

Yield: 5 g

The crude pyrimidine propenaldehyde (5 g) was dissolved in ethyl acetate (10 ml) at 20-25° C. and then added n-heptane (40 ml). The mixture was stirred for 2 h at 25-30° C. The resulting mass was cooled to 5° C. and stirred for 30 min at 0-5° C. Filtered the mass, washed with pre-cooled n-heptane (10 ml, 2° C.) and then dried under vacuum at 35° C. to give pure pyrimidine propenaldehyde.

Yield: 3 g

EXAMPLE 8

Preparation of (2E)-3-[4-(4-Fluorophenyl)-6-Isopropyl-2-(N-Methyl-N-Methylsulfonylamino)Pyrimidin-5-Yl]Propenal A crude mixture of alcohol IV and olefin V (5 g) was dissolved in N,N-dimethylformamide (20 ml) and treated with phosphorous oxychloride (20.8 g) at 0-5° C. The resulting reaction mass was allowed to stir for 12 h and heated at 80-85° C. for 24 h. After completion of the reaction, the reaction mass was poured on crushed ice and stirred for 1 h and the pH of this reaction mass was adjusted to 8.0-8.5 with aqueous sodium hydroxide. The product was taken in methylene chloride and worked-up as described in the example 7, to give crude pyrimidine propenaldehyde.

Yield: 5 g

The crude pyrimidine propenaldehyde (5 g) was recrystallized from ethyl acetate and n-heptane (2:8) to give pure pyrimidine propenaldehyde.

Yield: 3.5 g

We claim:

1. A process for the preparation of (2E)-3-[4-(4-fluorophenyl)-6-isopropyl-2-(N-methyl-N-methylsulfonylamino)pyrimidin-5-yl]propenal of Formula I,

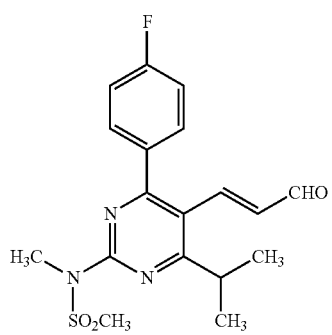

Formula I which comprises:
a) treating 4-(4-fluorophenyl)-6-isopropyl-2-(N-methyl-N-methylsulfonyl-amino)pyrimidin-5-yl]carboxaldehyde of Formula III,

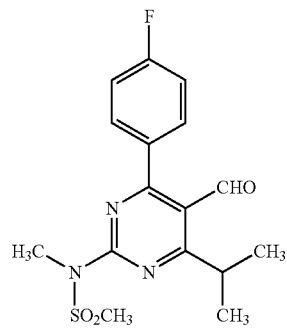

Formula III with an organometallic reagent to obtain a mixture of substituted ethanol of Formula IV and an olefin of Formula V;

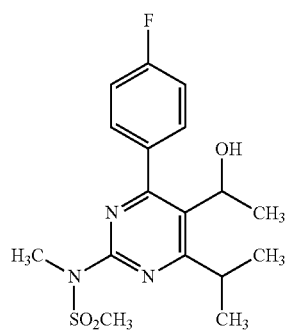

Formula IV

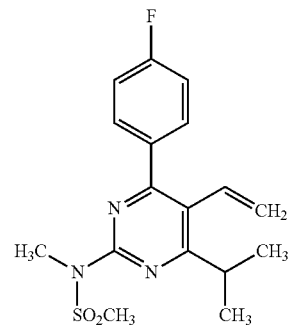

Formula V b) treating the mixture obtained above with Vilsmeier reagent; and
c) isolating the compound of Formula I.

2. The process according to claim 1, wherein the organometallic reagent used in step (a) is selected from $CH_3MX$ or $CH_3M$ or $(CH_3)_nM$; wherein M represents magnesium, lithium, zinc or cadmium; X represents chloro, fluoro, iodo or bromo; and n represents an integer 1 or 2.

3. The process according to claim 2, wherein the molar ratio of organometallic reagent based on pyrimidine carboxaldehyde is 1-10 moles.

4. The process according to claim 1, wherein the reaction in step (a) is carried out in an inert solvent selected from tetrahydrofuran, ether, toluene or mixtures thereof.

5. The process according to claim 1, wherein the Vilsmeier reagent is prepared from N,N-dimethylformamide and phosphorous oxychloride; N,N-dimethylformamide and oxalyl chloride; N-methylformanilide and phosphorous oxychloride or N-methylformanilide and oxalyl chloride in the presence of a solvent selected from the group consisting of dichloromethane, tetrachloromethane, 1,2-dichlorobenzene, ethylene dichloride and acetonitrile.

6. The process according to claim 5, wherein the organic base is selected from lutidine, tetramethylpyrazine or 2,6-dimethyl pyrazine.

7. The process according to claim 1, wherein the Vilsmeier reagent is prepared and added to the reaction mass or prepared in situ during the reaction.

8. The process according to claim 1, wherein the Vilsmeier reagent is added to the reaction mass ranging from 1 mole equivalent to 20 mole equivalents based on compound of Formula IV.

9. A process for the preparation of Rosuvastatin or pharmaceutically acceptable salts thereof from compound of formula I, wherein compound of formula I is prepared according to claim 1.

10. The intermediate of Formula IV

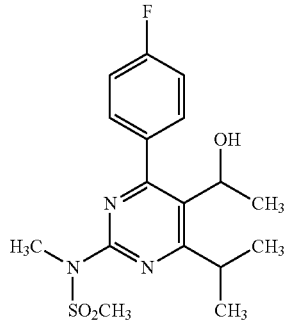

Formula IV is characterized by 1H NMR (300 MHz, CDCl$_3$): δ (ppm): 1.33 (dd, J=6, 12 Hz; 6H,—CH(CH$_3$)$_2$), 1.58 (d, J=6 Hz, 3H, CH$_3$), 1.76 (d, J=4.5 Hz, 1H, —OH), 3.51 (S, 3H, —NCH$_3$), 3.54 (s, 3H, —SO$_2$CH$_3$), 3.82-3.87 (m, 1H, —CH(CH$_3$)$_2$), 5.14-5.17 (m, 1H, —CHOH), 7.12-7.18 (m, 2H, ArH), 7.45-7.5 (m, 2H, ArH).

11. The intermediate of Formula V

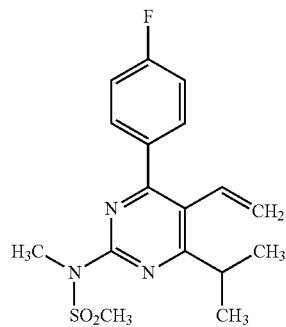

Formula V is characterized by $^1$H NMR (300 MHz, CDCl$_3$): δ (ppm): 1.29 (d, J=6 Hz, 6H,—CH(CH$_3$)$_2$), 3.44-3.51 (m, 1H, —CH(CH$_3$)$_2$), 3.54 (s, 3H, N-CH$_3$), 3.60 (s, 3H, 13 SO$_2$CH$_3$), 5.20 (dd, J=1.5, 17.7 Hz, 1H, =CH), 5.5 (dd, J=1.5, 11.4 Hz, 1H, CH=CH$_2$), 7.01-7.12 (m, 2H, ArH), 7.67-7.74 (m, 2H, ArH).

\* \* \* \* \*